United States Patent
McNair et al.

(10) Patent No.: US 12,176,093 B1
(45) Date of Patent: Dec. 24, 2024

(54) DECISION SUPPORT FOR MANAGING MENTAL HEALTH CONDITIONS

(71) Applicant: Cerner Innovation, Inc., Kansas City, KS (US)

(72) Inventors: Douglas S. McNair, Leawood, KS (US); John Christopher Murrish, Overland Park, KS (US); Kanakasabha Kailasam, Olathe, KS (US); William A. Stadler, Kansas City, MO (US); Pedro Alves, Overland Park, KS (US); Sasanka Are, Kansas City, MO (US)

(73) Assignee: Cerner Innovation Inc., Kansas City, MO (US)

( * ) Notice: Subject to any disclaimer, the term of this patent is extended or adjusted under 35 U.S.C. 154(b) by 720 days.

(21) Appl. No.: 14/982,993

(22) Filed: Dec. 29, 2015

Related U.S. Application Data

(62) Division of application No. 13/925,092, filed on Jun. 24, 2013, now abandoned.

(60) Provisional application No. 61/663,279, filed on Jun. 22, 2012.

(51) Int. Cl.
| | | |
|---|---|---|
| *G16H 20/70* | (2018.01) | |
| *G16H 40/67* | (2018.01) | |
| *G16H 50/50* | (2018.01) | |

(52) U.S. Cl.
CPC ............ *G16H 20/70* (2018.01); *G16H 40/67* (2018.01); *G16H 50/50* (2018.01)

(58) Field of Classification Search
None
See application file for complete search history.

(56) References Cited

U.S. PATENT DOCUMENTS

| | | |
|---|---|---|
| 4,675,904 A | 6/1987 | Silverman |
| 5,148,483 A | 9/1992 | Silverman |
| 5,976,081 A | 11/1999 | Silverman |

(Continued)

FOREIGN PATENT DOCUMENTS

| | | | | |
|---|---|---|---|---|
| CN | 102037355 A | * | 4/2011 | ........... C12Q 1/6883 |

OTHER PUBLICATIONS

Dienes, Kimberly Ann. "The Biopsychosocial Model of Risk for Depression." Order No. 3335903 University of California, Los Angeles, 2008. Ann Arbor: ProQuest. Web. Oct. 2, 2024. (Year: 2008).*

(Continued)

*Primary Examiner* — Lena Najarian
(74) *Attorney, Agent, or Firm* — Kilpatrick Townsend & Stockton LLP

(57) ABSTRACT

Methods, systems, and computer-readable media are provided for managing health status of persons with a chronic condition including providing dynamic, adaptive monitoring, detection, and prediction of suicide risk to a person at risk for suicide related to mental health. In an embodiment, a patient-assessment application is used to obtain information periodically on a patient's mental health status. Based on this information, a logistic regression model is employed to determine a patient's probability of attempting suicide. The probability is evaluated against a default threshold to determine if the patient's status has changed significantly, and if the threshold is exceeded, an action is evoked. In one embodiment, the action includes providing notice to the patient's care provider, caregiver, or case manager.

20 Claims, 8 Drawing Sheets

(56) References Cited

U.S. PATENT DOCUMENTS

| | | | |
|---|---|---|---|
| 7,062,443 B2 | 6/2006 | Silverman et al. | |
| 7,139,699 B2 | 11/2006 | Ozdas et al. | |
| 7,454,350 B2 | 11/2008 | Silverman | |
| 7,565,285 B2 | 7/2009 | Ozdas et al. | |
| 2002/0072970 A1 | 6/2002 | Miller et al. | |
| 2003/0059750 A1 | 3/2003 | Bindler | |
| 2003/0078768 A1 | 4/2003 | Silverman et al. | |
| 2006/0202816 A1* | 9/2006 | Crump | A61B 5/0022 600/300 |
| 2006/0212484 A1* | 9/2006 | Chaffin | G16H 10/60 |
| 2007/0244375 A1 | 10/2007 | Jenkins | |
| 2008/0146888 A1 | 6/2008 | Azzaro et al. | |
| 2008/0201172 A1* | 8/2008 | McNamar | G16H 10/40 705/3 |
| 2008/0287746 A1* | 11/2008 | Reisman | G16H 40/63 600/300 |
| 2010/0016751 A1* | 1/2010 | Hunter | A61B 5/0476 600/544 |
| 2011/0145013 A1* | 6/2011 | McLaughlin | A61B 5/00 705/3 |
| 2011/0231208 A1* | 9/2011 | Kaplin | G06F 19/3418 705/3 |
| 2011/0245092 A1* | 10/2011 | Bilello | C12Q 1/6883 506/8 |
| 2011/0257561 A1* | 10/2011 | Gertner | A61N 7/00 600/407 |
| 2012/0060851 A1 | 3/2012 | Amberg | |
| 2012/0083666 A1 | 4/2012 | Waugh et al. | |
| 2012/0201747 A1* | 8/2012 | Altschul | A61K 9/107 977/773 |
| 2012/0245479 A1 | 9/2012 | Ganesh et al. | |
| 2012/0314901 A1* | 12/2012 | Hanson | A61B 5/0077 382/103 |
| 2013/0060580 A1 | 3/2013 | Chapman et al. | |

OTHER PUBLICATIONS

Non-Final Office Action dated May 30, 2017 in U.S. Appl. No. 13/925,092, 18 pages.

First Action Interview Office Action, U.S. Appl. No. 13/925,092, dated Feb. 9, 2016, 5 pages.

Office Action dated Jun. 20, 2018 in U.S. Appl. No. 13/925,092, 16 pages.

Final Office Action dated Jan. 17, 2018 in U.S. Appl. No. 13/925,092, 14 pages.

Final Office Action received for U.S. Appl. No. 13/925,092, mailed on Jul. 12, 2016, 18 pages.

Final Office Action received for U.S. Appl. No. 13/925,092, mailed on Feb. 15, 2019, 16 pages.

Non-Final Office Action received for U.S. Appl. No. 13/925,092, mailed on Sep. 27, 2019, 17 pages.

\* cited by examiner

Example In-patient suicide risk prediction process and data flow (continued)

|  | sui+ | sui- |
|---|---|---|
| pred_sui+ | A | B |
| pred_sui- | C | D |

~402

ODDS RATIO (OR) = AD/CB

95% PI OF LN(OR) = LN(OR) ±1.96*(1 + 1/1)$^{0.5}$*(1/A + 1/B + 1/C + 1/D)$^{0.5}$

OBSERVATIONAL COHORT
1,954

|  | sui+ | sui- |
|---|---|---|
| pred_sui+ | 736 | 416 |
| pred_sui- | 322 | 480 |

~402

|  |  | LN(*) | S.E LN(*) |
|---|---|---|---|
| +95% OR | 3.43 | 1.232 |  |
| OR | 2.64 | 0.970 | 0.185 |
| -95% OR | 2.03 | 0.708 |  |

*FIG. 4*

DECISION SUPPORT FOR MANAGING MENTAL HEALTH CONDITIONS

CROSS-REFERENCE TO RELATED APPLICATIONS

This application is a divisional of U.S. patent application Ser. No. 13/925,092, filed Jun. 24, 2013, entitled "Decision Support For Managing Mental Health Conditions," which claims priority to U.S. Provisional Application No. 61/663, 279, entitled "Decision Support For Managing Mental Health Conditions," filed Jun. 22, 2012. The aforementioned applications are hereby incorporated by reference herein.

BACKGROUND

In the United States in 2009, there were approximately 634,000 in-patient admissions to mental health facilities related to self-harm and/or attempted suicide. Large multi-institution networks of hospitals such as Universal Health Systems are responsible for the care of a major percentage of these patients. A percentage of patients admitted to such institutions with these reasons-for-admission undertake a suicide attempt during the in-patient episode, and a percentage of these attempts result in completed suicides. In addition, some patients who are admitted to mental health institutions for treatment of chemical dependency or other conditions and who have no prior history of self-injury or attempted suicide, do attempt suicide for the first time in the hospital after having been admitted.

In an attempt to address the problem, intensified monitoring ('close-observation' policies) and observation procedures have become increasingly common in recent years, either as a result of professional society or quality assurance organization initiatives or as a result of adverse judgments in court cases involving in-patient deaths by suicide. However, the protective efficacy of close observation during in-patient mental health admissions is uncertain and even a high level of observation may be ineffective in preventing suicide attempts in patients who are determined to leave the ward to which they have been admitted. Additionally, the incremental expense entailed by intensified monitoring implemented on 100% of patients, including a large portion of the patients for whom it is not truly needed, yields dramatically increased expense to provide mental health in-patient services.

SUMMARY

Systems, methods, and computer-readable media are provided for facilitating monitoring and managing the mental health conditions of persons at risk for suicide or for assessing mental health conditions of a plurality of geographically disperse patients. In particular, embodiments of the invention enable health-care providers to automatically and easily monitor one or more mental health conditions; to automatically estimate statistically significant probability of suicide attempt via measurements of one or more variables pertaining to the mental health conditions associated with risk of suicide while admitted for in-patient care; to facilitate timely communication regarding a detected trend or emerging pattern indicative of increased risk; and to facilitate effective patient behavior modification in remotely located patients by providing timely rewards for correct behavior. In some embodiments, a logistic regression model is employed for classification.

In particular, in some embodiments, information is transmitted from a patient monitoring system to a computer system, or data processing system, and analyzed substantially simultaneously with the transmission thereof (1) to identify materialized changes in health status requiring immediate medical attention and (2) to predict incipient transgressions of established thresholds, which may be established to trigger intervention to prevent certain exacerbation events, such as deterioration in psychiatric condition as may make suicide attempt more likely. For such changes and predicted boundary transgressions, alerts or notifications may be automatically communicated to the respective patient monitoring system or to other systems, such as the electronic health record system utilized for case management, or to a case manager, physician, caregiver, or family member, such as via an electronic mail account or cellular telephone, in some embodiments.

In some embodiments, methods, systems, and computer-readable media are provided for facilitating monitoring and assessing mental health of a plurality of geographically dispersed patients using a computer system, or data processing system that may either be centralized or may use a cloud-based, virtual configuration of services. In some embodiments, the system is configured to communicate with and receive data from one or a plurality of respective patient-assessment applications. Patient-assessment applications, patient-assessment devices, or patient-monitoring devices, include monitoring devices, electronically based assessment devices or applications, and computer- or smart-phone-based assessment applications, apps, or applets capable of receiving and facilitating storage of information corresponding to a patient's condition and may also include a means of uploading or transferring stored measurement information and corresponding date-time coordinates for each assessment or measurement to a data processing computer system.

In some embodiments, the data processing system can be configured to obtain patient information from each patient assessment application, to analyze the obtained patient information, and to identify patterns meriting attention by the patient, by caregivers, by case managers, or by the physician. Some embodiments also track each identified change or predicted transgression for a patient from identification to response. Further, some embodiments may track whether or not a case manager or other user has communicated information to a patient or caregiver regarding a detected or predicted event. In addition, some embodiments track whether or not a patient has received the communication initiated by a case manager or other supervisory user who is responsible for administering health services.

According to one aspect, a method or system is provided for monitoring patient assessments of a plurality of remotely located patients that includes a data processing computer system configured to communicate with a plurality of patient assessment applications and a remotely located client in communication with the data processing computer system. In embodiments, the computer system may be configured to obtain patient information from one or more of the assessment applications and to analyze the obtained patient information to identify statistically significant changes in the mental health status of each respective patient.

According to another aspect, a method or system is provided for facilitating, monitoring, and managing in-patient health care for patient at risk for suicide. For example, specific levels of observation can be dynamically tailored to an individual patient based on a process of ongoing assessment and reassessment of suicide risk throughout the in-patient admission. In particular, the first few days post admission are a time of elevated suicide risk, and increased-intensity observation protocols may be justified during this interval. In the case of patients at high or very high risk of suicide attempt, embodiments of the invention incorporating software-based clinical decision-support services can apply greater priority to other care plan interventions besides monitoring. This might include, for example, movement of the patient into a locked ward or into an 'increased monitoring-intensity' area, placing the patient in physical restraints, or engaging family members during the in-patient episode, since family members are known to play a crucial role in encouraging patients to comply with treatment protocols, and to return to the hospital if they have absconded.

According to another aspect, a method for monitoring a mental health condition of a patient is provided, where the method includes receiving over a span of time, a series of assessment information including a determined level for a variable associated with a patient's mental health condition, thereby forming a timeseries. The method also includes determining an event that is indicated by the timeseries; the event corresponding to an increased probability for patient suicide. The method further includes evoking an action corresponding to the determined event.

According to another aspect, a method is provided for facilitating treatment of a population of geographically disperse patients having a mental health condition, wherein the method includes administering selected interventions to a set of members of the population who exhibit above-threshold values of a predictive score calculated from a variable associated with an exacerbation in the mental health condition. In some embodiments of the method, the predictive score is determined based on timeseries of determined levels for a variable associated with the mental health condition, and in some embodiments the predictive score comprises a probability for attempting suicide with a ninety-five percent prediction interval. In some embodiments, the predictive score is determined using logistic regression. In some embodiments, the levels for the variable are determined by a patient assessment including observationally determined or measured variable-level assessments. In some embodiments, the threshold is determined based on the variable and the mental health condition, and wherein the threshold is satisfied when the predictive score exceeds the threshold.

According to another aspect, a method is provided for monitoring a mental condition of a patient to prevent deterioration, wherein the method includes receiving information based on patient variable values from a patient assessment for determining a value of a variable associated with a mental health condition, and generating a timeseries from the received information. The method also includes determining a change pattern in the timeseries representing a level of change in values of the variable. The method further includes performing a comparison of the level of change to a threshold and based on the comparison, determining that the level of change satisfies the threshold, generating a response. In some embodiments, the threshold is satisfied when the level of change exceeds the threshold.

Accordingly, some embodiments are particularly well-suited for facilitating patient behavior modification, by enabling them or their caregivers to be automatically notified of emerging changes, such that they experience an incentive to interdict the trends or changes by improving their adherence to the prescribed plan of care or by initiating contact with their clinicians to seek an adjustment of the plan of care. Such embodiments are especially germane to the situation of mental health provider organizations subject to oversight by public health and accreditation organizations and compliance with regulations pertaining to adverse outcomes prevention.

BRIEF DESCRIPTION OF THE DRAWINGS

Embodiments of the invention are described in detail below with reference to the attached drawing figures, wherein:

FIG. 4 illustratively provides example calculation results from an embodiment of a method using logistic regression to determine a probability of suicide attempt.

DETAILED DESCRIPTION

Figure 1A:
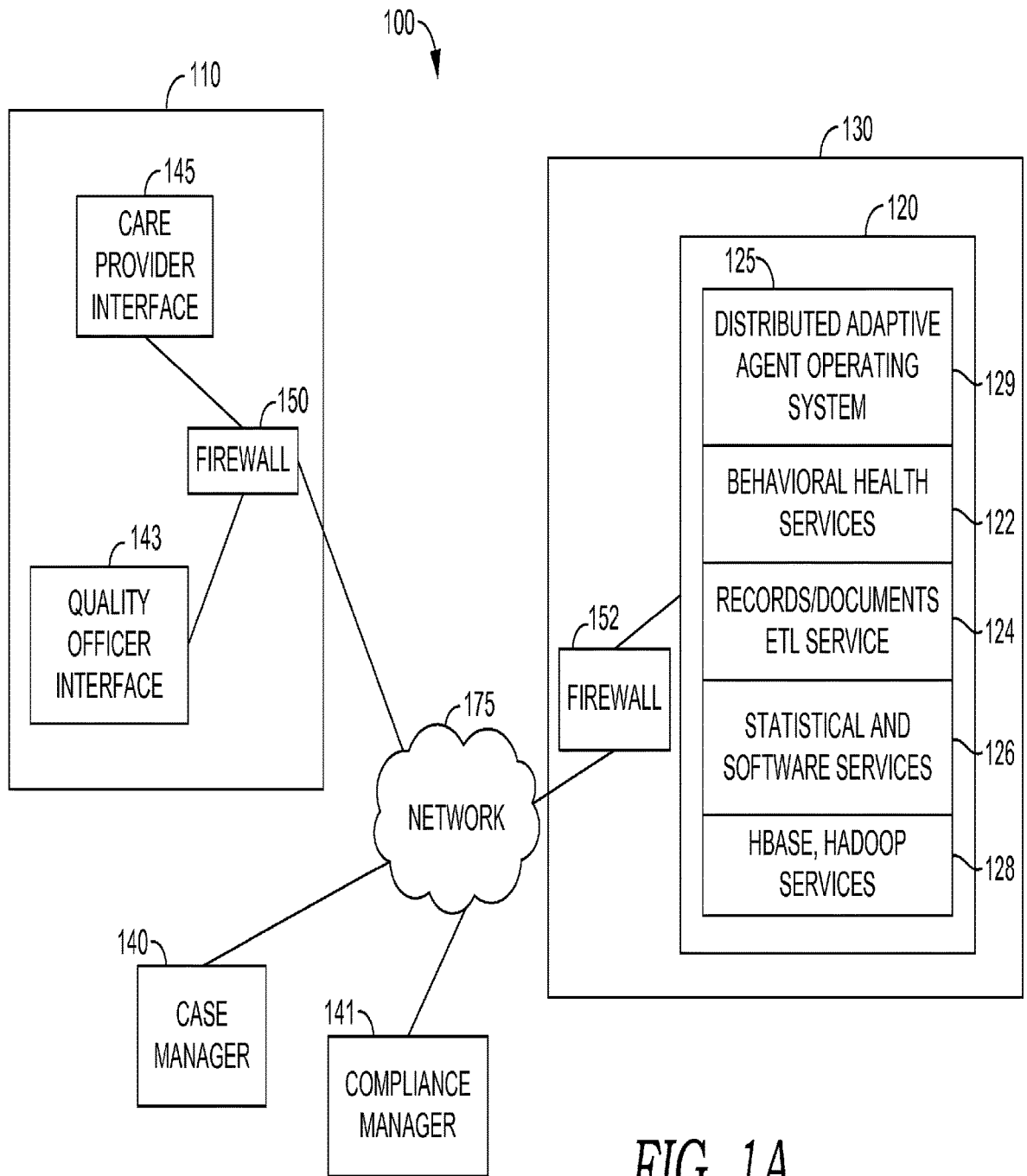
FIGS. 1A, 1B, and 1C depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things, a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

As discussed above, embodiments of the invention are provided for, among other purposes, facilitating monitoring and managing the health status of persons with mental health conditions including persons at risk for suicide. Among the many clinical decisions psychiatrists must make, assessment of a patient's risk of committing suicide is definitely among the most complex and demanding; identification of individuals at imminent suicidal risk is the most important decision a clinician makes. Currently, such assessment is done on a clinical intuitive level, which requires gathering and weighing a variety of information and data from numerous sources. This data includes the patient's demographic profile, history, family evaluation and psychological factors, as well as the current situation as evaluated during the clinical interview. This data helps categorize groups of people as "high risk" but the data is not useful to determine if a patient is at imminent risk. Moreover, collecting such data is time consuming; required data to make a decision is usually not available in clinical situations requiring an immediate decision.

Additionally, there are presently no generally accepted, objective diagnostic tools or predictive instruments to supplement routine clinical judgment for quantitative determination of the magnitude of near-term suicidal risk in patients treated as in-patients in mental health facilities. This is partly because most of the variables that are readily available by default (age, health status, race, socioeconomic status, etc.) associated with near-term risk (a) are difficult to generalize to a large population of mental health in-patients and (b) together explain a low percentage of the variance (<30% in univariate analysis of variance).

Furthermore, conventional approaches for monitoring and preventing suicide attempts have several additional limitations, including:

(1) Failure to accommodate or measure interobserver variation in the measurements used in the assessment and statistical predictive model;

(2) Repetitively or intrusively readministering an assessment protocol, such as induces annoyance and noncompliance on the part of the patient being evaluated;

(3) Failure to replicate the assessment to detect time-dependent changes and variations in observations or patient clinical findings (e.g., suicidal ideation; delusional ideation) over the course of the in-patient admission;

(4) In approaches, which monitoring at-risk patients by analyzing wavelet or other signal processing of digitized vocal waveforms of patients' speech, there is required expensive and complex equipment, special skill in administering the tests and processing the speech waveform record, and cooperation from the patient (who might not verbalize the utterances required by the assessment method, or might do so in a noncompliant manner such as will generate false-positive or false-negative prediction errors);

(5) Limited mobility, portability and convenience, in particular some conventional approaches using computer systems and software require the provider to take along equipment if they are mobile within an institution or outside it; and (6) Failing to recognize that suicide attempts are a stochastic event process that can be well-fit by a Poisson Distribution. Specifically, the prevalence of suicide by in-patients in psychiatric hospitals is less than 5% in large cohorts, and the predictors have low sensitivity and low positive predictive value (PPV<10%), which is too low to support safely and confidently ruling-out a suicide attempt in the "N-of-1" individual-patient application use case.

Accordingly, embodiments of the present invention provide systems and methods for dynamic, adaptive monitoring, management, and prediction of persons at risk of suicide generally, and in particular persons at risk of suicide with one or more mental health conditions while treated in an in-patient setting, which mitigate the aforementioned limitations. Furthermore, some embodiments of our invention use assessment instruments that collect additional variables that have greater variance-explanatory power. Some embodiments of the invention are provided for facilitating monitoring and managing the health status of persons with any chronic health condition, such as mental health conditions of persons at risk for suicide, sepsis, or sequential organ failure. At a high level, these embodiments involve applying a classification model, such as logistic regression method, for determining a patient's likelihood of committing suicide or having a particular condition, such as sepsis.

In particular, as discussed above, some embodiments provide a system and method for monitoring serial quantitative measurements made of one or more demographic and mental health assessment variables in a person, comprising: (a) acquiring and storing measurements from an assessment application, such as an online software application including an assessment data-entry form; (b) transferring the assessment values from the client application to an electronic health record system; (c) detecting whether the measurements of the variable or plurality of variables for the individual patient merits intervention by one or more individuals who are responsible for the care of the person, (d) notifying one or more from a set of individuals who have responsibility for the care of the patient and/or responsibility for risk management and regulatory compliance of the health care institution, wherein the set may include other caregivers, or one or more health plan case managers or quality or risk-management officers, and (f) tracking and storing a notification event and the status and time of response or nonresponse by a caregiver to the notification.

In some embodiments, the detection step is carried out by applying a classification method, such as logistic regression classification, for determining a patient's likelihood of committing suicide. In particular, in some embodiments, logistic regression is applied to determine the probability of a suicide attempt with a ninety-five percent confidence interval for a given sample size N, such as N=1. A confidence interval such as this can serve as a prediction interval for determining whether or not a particular patient is likely to commit suicide and further, whether the patient's mental health status is improving or degenerating, and whether or not to evoke an action such as providing notice to a caregiver. In some embodiments, the probability P is given as $P=\exp(\beta_0+\beta_1 x)/(1+\exp(\beta_0+\beta_1 x))$, wherein $\beta_1=\ln(OR)$, $\beta_0$=the default rate of suicides, and OR, the odds ratio, is given as $OR=AD/CB$, where A is the count for prediction that a suicide attempt is likely that resulted in a suicide attempt; B is the count for prediction that a suicide attempt is likely that resulted in no suicide attempt; C is the count for prediction that a suicide attempt is not likely that resulted in a suicide attempt; and D is the count for prediction that a suicide attempt is not likely that resulted in no suicide attempt. Accordingly, a ninety-five percent prediction interval, 95% PI, when sample size N=1, is then given as: 95% of $\ln(OR)=\ln(OR)\pm 1.96 \ (1+1/1)^{0.5} \ (1/A+1/B+1/C+1/D)^{0.5}$.

Further details of this example are described below and provided in connection to FIG. 4.

In such ways, embodiments of the invention provide advantages including enabling physicians, case managers, family member caregivers and other health-care providers to remotely monitor, identify, and manage a patient's mental health conditions, thereby (1) obviating the need for frequent, intensive monitoring in those patients who are in fact at low risk of suicide and (2) enabling the effective reallocation of available capacity to intensive monitoring of those patients who are at increased risk of suicide. In embodiments employing a logistic regression classification model, additional advantages are provided by the model's high specificity and high negative predictive value (NPV), such that, if risk is determined to be low, an "N-of-1" statistical prediction interval bounding the predicted probability is also suitably narrow for the individual-patient application; thus monitoring labor may be safely reduced. Furthermore, some embodiments compute an "N-of-1" statistical prediction interval for the predicted probability of suicide attempt such that interobserver variation in measurement or interpretation of the variables included in the model is taken into account in a statistically valid manner.

Additional advantages provided by embodiments include enabling physicians, case managers, family member caregivers and other health-care providers to communicate in a timely manner regarding the detected trend or emerging pattern; facilitating effective patient behavior modification in remotely located patients by providing timely rewards for correct behavior; and enabling assessment-application manufacturer-agnostic uploading and analysis, so that assessment application values of a particular type are uniformly deposited in the electronic health record and are retrievable for analysis under a unified taxonomy or ontology, such that the workflow is consistent for the user regardless which software, manufacturer, or device model deposited the values (provided, in some cases, that the consumer, caregiver or health-care provider has conformed to the manufacturer's calibration or other procedures required to insure the accuracy of the results).

Some embodiments of the invention are also advantageous because physicians, case managers, family member caregivers, and other health-care providers can monitor, identify, and manage a patient's mental health condition. Furthermore, some embodiments facilitate resources-conserving automation of various aspects of preventive services provisioning. In addition, physicians, case managers, and family members utilizing embodiments may be able to quickly discern whether or not a patient is experiencing a change in the severity of a mental health condition requiring immediate attention, and distinguish that situation from a minor fluctuation that does not merit intervention and from fluctuations that are within the range of normal for that patient.

Turning now to FIG. 1A, there is presented in 100 an example operating environment suitable for practicing embodiments of the invention. Example operating environment 100 includes a computerized system for compiling and running an embodiment of a decision support recommendation service. With reference to FIG. 1A, a first premise location 110 includes a network behind firewall 150 communicatively coupled to Network 175. Premise location 110, which may comprise separate geographical locations, includes care provider interface 145 and quality officer interface 143. Embodiments of care provider interface 145 include a software application, device or sensor capable of monitoring, measuring, or receiving information about a patient including one or more variables that relate to the patient's health status. In some embodiments, care provider interface 145 takes the form of a patient-assessment application. In some embodiments, care provider interface 145 is located in the patient's home, in an ambulatory setting, in an in-patient setting, or in possession of the patient, and in some embodiments care provider interface 145 is worn by the patient, embedded within the patient, or otherwise affixed to the patient. For example, care provider interface 145 might take the form of a software application, app, or Web applet running on a computing device such as a laptop, smartphone, tablet, distributed computer system, or other computer system including a system such as described in connection to FIG. 1C; a camera; a motion sensor, including for example home-entertainment devices such as Microsoft® Kinect®, Sony® Move®, or Nintendo® Wii®; an eye-tracker; pedometer, accelerometer, movement or activity measuring device, including for example, the Nike® Fuel Band™ manufactured by Nike® Corporation, or a smartphone having accelerometer-detecting or gyro-detecting functionality and an application program (i.e., app) to facilitate monitoring, measuring, or receiving information about a patient; a Fitbit® device or smartphone application manufactured by the Fitbit® corporation, including for example, the Fitbit Sleep Tracker and Fitbit Ultra pedometer; a Zeo™ sleep sensor, manufactured by Zeo Inc. of Newton, Massachusetts; or another suitable application, device or interface capable of receiving information about one or more variables associated with the patient's condition. One such example embodiment of care provider interface 145 is a software application assessment form, which can be completed by a caregiver. An illustrative screenshot shows an example of aspects of such an assessment application in FIG. 3. Examples of variables that can be used in embodiments of the present invention include: diurnal peak and trough cortisol levels; norepinephrine, vanillyl mandelic acid, and homovanillic acid levels; pedometer-measured cumulative steps per day; pedometer or patient-sensor frequency of docking; fluid intake and output per day, such as by questionnaire or direct measurement; nutritional intake per day, such as by diet questionnaire or direct observation; medication regimen adherence behavior, which in one embodiment may be measured by web-connected smart medicine containers that detect medication-taking or non-adherence; therapeutic drug monitoring drug levels, and in some embodiments in particular, phenothiazines and other neuroleptics; free ionized calcium level; IL-6, IFN-gamma, TNF-alpha, and other cytokine levels; electroencephalography (EEG) measures including evoked potentials; EEG somnography or sleep actigraphy, which can be measured using Fitbit, Zeo, or other patient sensors or monitoring applications; electrocardiogram measures, including heart rate variability (HRV) and spectral analysis of EKG; facial electromyography measures; skin conductance; genetic and epigenetic markers; behavioral measures, such as cue-exposure and challenge tests; functional magnetic resonance imaging (fMRI) or 18F-dG PET imaging of the brain; or other such physiological (including cognitive) or physical-activity related variables.

Figure 3:
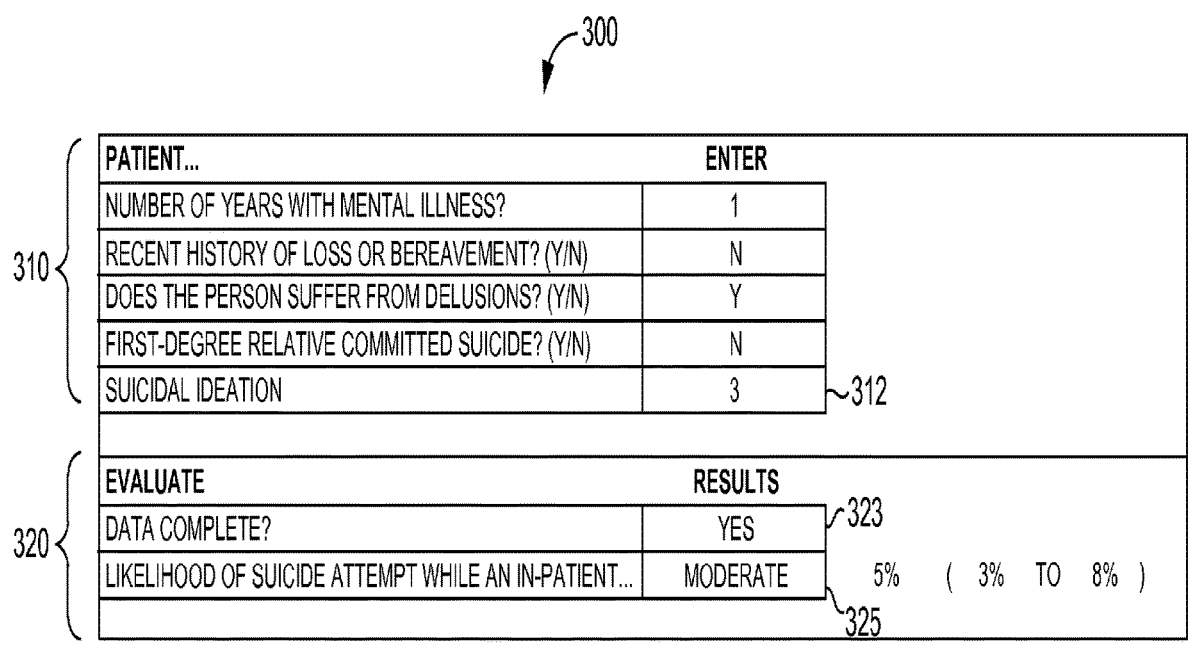
FIG. 3 depicts an illustration of an embodiment of a patient-assessment application in the form of a software-based, online patient status assessment form.

Turning now to FIG. 3, an illustrative depiction of an embodiment of a patient-assessment application is provided, which is generally referred to herein as 300. This embodiment of assessment application 300 is a patient assessment form, which operates on a computer system. In some embodiments, assessment application 300 is a Web-based applet or application that operates inside a browser or an app operating on a mobile computing device such as a smartphone or tablet. In the embodiment of which aspects are illustratively depicted in FIG. 3, assessment application 300 includes an input component 310 for entering information about a particular patient. Such information may be provided by a care provider or case manager, and may be done on a daily basis. In some embodiments, the form may be limited to a small number of questions or fields of information about a patient, rather than an extensive interrogation of the patient, because such extensive interrogations may result in aggravating the patient's condition. In some embodiments, the person entering information into the patient assessment may enter numbers into a field or click or select buttons, such as software radio buttons, which may correspond to numerical values on a Likert scale. For example, assessment application 300 includes a suicidal ideation value 312, which may be provided by selecting radio buttons corresponding to a Likert scale of three to five levels. In some embodiments, assessment application 300 is linked to a measuring device such that readings taken from the device are used to populate fields of assessment application 300. Similarly, in some embodiments, a patient electronic health record (EHR) is linked to or otherwise associated with assessment application 300 so that some fields may be automatically populated by accessing information from the patient's EHR.

In some embodiments, assessment application 300 also includes a results component 320, which provides an assessment of patient's health status. For example, in the embodiment of FIG. 3 an indication of whether or not the all input data is complete is provided in 323. Thus, the caregiver can be made aware that additional patient information needs to be provided in input component 310. Results component 320 can also include an output 325 of the determination of the patient's risk for committing suicide (or determination of the likelihood that the patient has a particular condition, such as sepsis). In some embodiments, a raw number, such as the prediction interval, is provided in 325. Alternatively, in some embodiments, a word-description or color, corresponding to the determined likelihood, is provided. For example, in the embodiment shown in FIG. 3, output 325 shows a "Moderate" likelihood that the patient will commit suicide. Examples of word descriptions associated with the determined likelihood that the patient has a condition might include: Moderate, Slight, Low, High, Very Low, or Very High, for example. Similarly, colors such as green, yellow, red or other colors could be used to denote the patient's likelihood of having the condition, where red might correspond to a high determined likelihood and green to a low determined likelihood, in one embodiment.

Returning to FIG. 1A, in some embodiments, care provider interface 145 facilitates automatically communicating received patient information to a patient's EHR by way of network 175, such as by uploading information after each assessment session. In some embodiments, care provider interface 145 includes functionality for wireless communicative-coupling, such as for example Bluetooth, cellular, Wi-Fi or other suitable wireless communications technologies, and in some embodiments, care provider interface 145 includes USB-connectivity.

In some embodiments, care provider interface 145 facilitates local storage, access, or communication of the information received. In some embodiments, information is communicated to an electronic health record (EHR), or to computer system 120, described below. In some example embodiments, care provider interface 145 uses the Cerner CareAware iBus® interface software.

Quality officer interface 143 facilitates monitoring, measuring, or receiving information about a patient including one or more variables that relate to the patient's condition. In some embodiments, quality officer interface 143 enables a quality officer or health-care provider to monitor an existing patient assessment application or to provide a patient assessment application, in a manner similar to care provider interface 145. Care provider interface 145 and quality officer interface 143 may be located in separate locations; each communicatively coupled to network 175, or may be mobile and change location, in some embodiments, or may reside on the same device.

In embodiments, network 175 includes the Internet, a public network, or a private network. In embodiments having a firewall 150, the firewall 150 may reside on the same computing device as care provider interface 145 or may comprise a separate firewall associated with care provider interface 145 and quality officer interface 143.

Example operating environment 100 further includes computer system 120, which may take the form of a data processing system or a server, within premise 130, which is communicatively coupled through firewall 152 and network 175 to care provider interface 145 and quality officer interface 143, in premise location 110, and also to case manager 140 and compliance manager 141. In embodiments, case manager 140 and compliance manager 141 may each take the form of a software application operating on one or more mobile computing devices, tablets, smartphones, front-end terminals in communication with back-end computing systems terminals, laptops or other computing devices. In some embodiments, case manager 140 and compliance manager 141 each includes a Web-based application or collection of applications that is usable to manage services provided by embodiments of the invention. In some embodiments, case manager interface 140 and compliance manager 141 are located or accessed on the same computer system. In some embodiments, case manager 140 and compliance manager 141 are part of the same software application. In some embodiments, case manager 140 and compliance manager 141 are located or accessed on the same computer system. In some embodiments, case manager 140 and compliance manager 141 are carried out by agents on a distributed multiagent or adaptive agent operating system as described in connection to computer system 120, below.

Figure 1B:
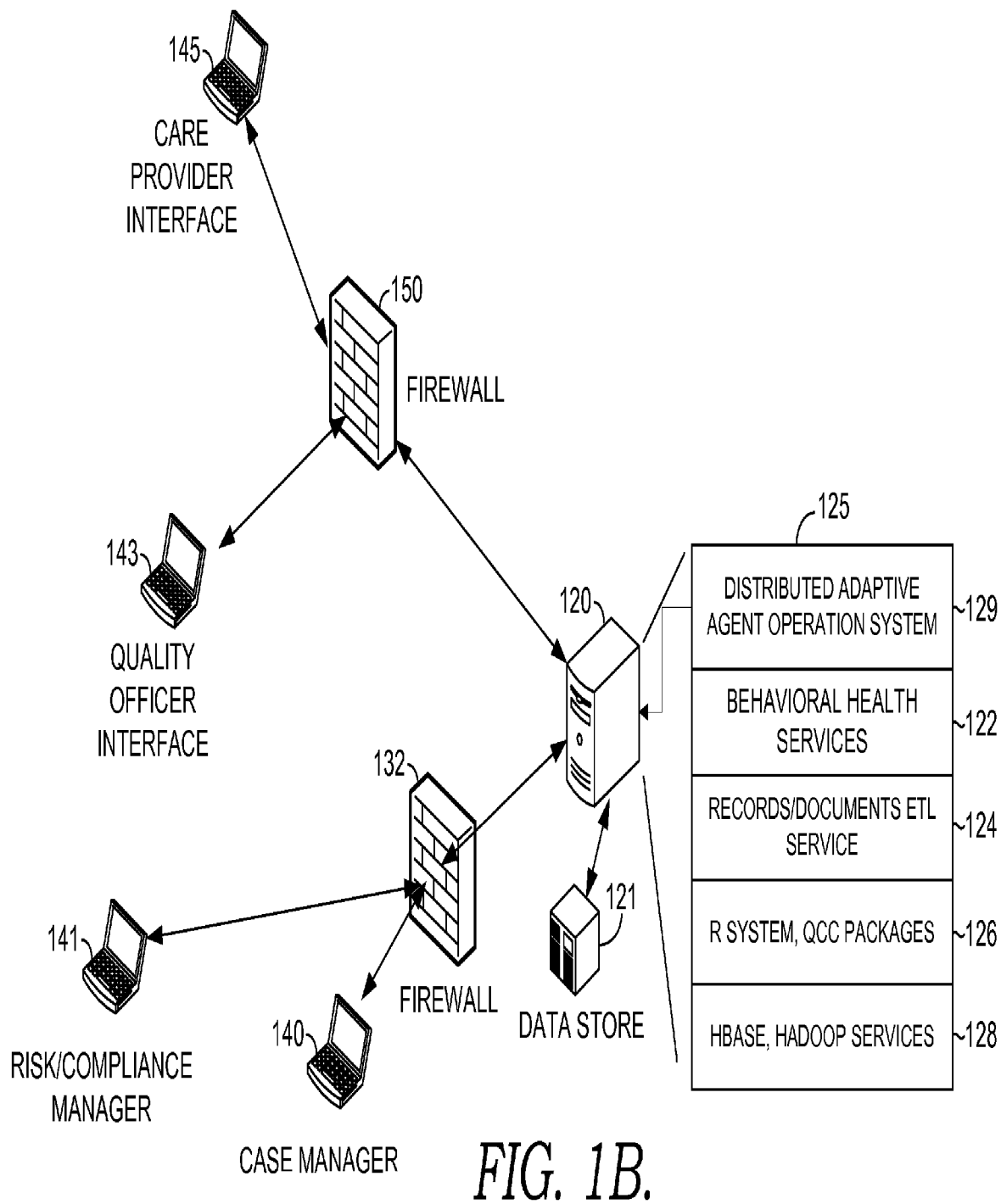

Embodiments of computer software stack 125 run on a computer system such as 120 shown in FIGS. 1A and 1B. Embodiments of software stack 125 may run as a distributed system on a virtualization layer within computer system 120. In some embodiments, computer system 120 includes a server cluster running an operating system such as Linux. Embodiments of software stack 125 can include a distributed adaptive agent operating system 129 that can host a number of services such as 122, 124, 126, and 128. In some embodiments, operating system 129's hosted services include cloud-based services. Embodiments of services 122, 124, 126 and 128 run as a local or distributed stack on a collection of personal computers and servers such as 120 and/or a computing device running manager interface 140. In one embodiment, case manager 140, compliance manager 141, or both operate in conjunction with software stack 125. Behavioral health services 122 can include services, which may include cloud-based services for facilitating health management by patient, health-care provider, or insurance provider including for example, health exchange services; health records, transaction, billing, and record-keeping services; information-technology services; or other services such as those provided by Cerner Healthe™ and Healthe Intent™. Furthermore, in some embodiments, operating system 129 and behavioral health services 122 provide services (including could-based services) for persistent data storage and retrieval, adaptive agent services, and time-out detection services.

Records/Documents ETL service 124 can provide services that facilitate retrieving frequent item sets, extracting database records, and cleaning the values of variables in records. In some embodiments, ETL service 124 provides services that facilitate the capturing, processing, storing, analyzing, and viewing of information obtained by care provider interface 145 and related information, such as, for example, electronic medical record (EMR) information about a particular patient or set of patients, and metadata such as user settings and metrics. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org). Embodiments of services 128 include Apache Hadoop and Hbase framework that provide a distributed file system.

FIG. 1B illustratively depicts another aspect of an example operating environment. Some of the components of FIG. 1B are described above with respect to FIG. 1A. Also shown in FIG. 1B is data store 121, which in some embodiments, includes patient data and information for one or more patients including information obtained via care provider interface 145; variables associated with recommendations; recommendation knowledge base; recommendation rules; recommendations; recommendation update statistics; operational data store, which stores events; frequent itemsets (such as "X often happens with Y," for example) and itemsets index information; association rulebases, agent libraries, and other information; patient-derived data, healthcare provider information, for example. Although depicted as a single data store, data store 121 may comprise more than one data store in one or multiple locations, or in the cloud. The example operating environment of FIG. 1B also includes a firewall 132 between case manager interface 140, compliance manager 141, and computer system 120. As described previously, firewalls 132 and 150 of FIG. 1B and also firewall 152 of FIG. 1A may reside within one or both of the components shown communicatively coupled to the firewall, or reside on an intermediate component such as a server. It is contemplated that some embodiments do not include firewalls.

Figure 1C:
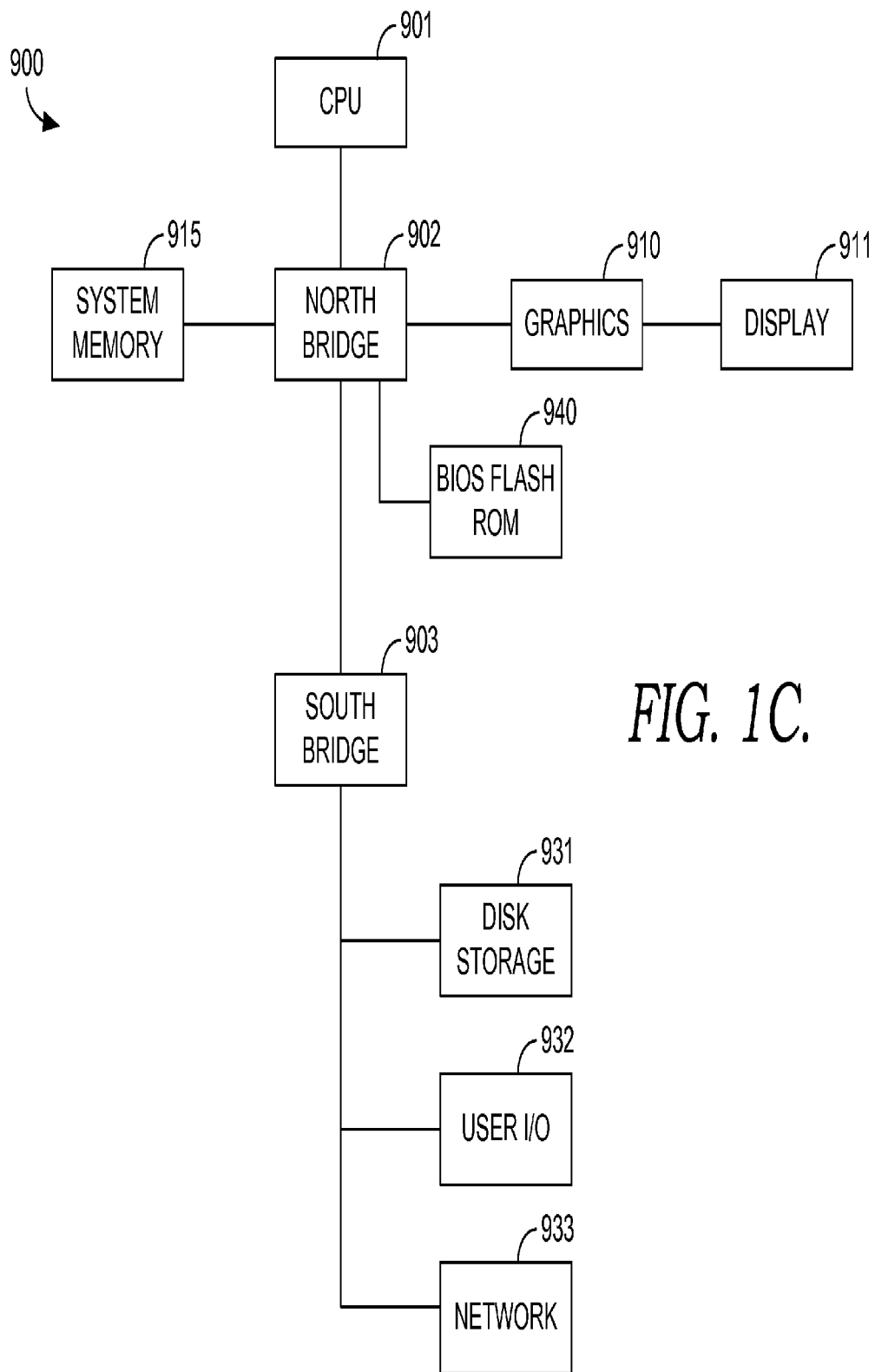

Turning now to FIG. 1C, there is shown one example of an embodiment of computer system 900 that has software instructions for storage of data and programs in computer-readable media. Computer system 900 is representative of a system architecture that is suitable for computer systems such as system 120 and the computer device(s) operating manager interface 140 and care provider interface 145. One or more CPUs such as 901 have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902 allowing CPU 901 to store instructions and data elements in disk storage 931 such as a fixed disk or USB disk, or to make use of network 933 for remote storage. User I/O device 932 (such as a communication device, a mouse, a touch screen, a joystick, a touch stick, a trackball, or keyboard) couples to CPU through south bridge 903 as well. The system architecture depicted in FIG. 1C is provided as one example of any number of suitable computer architectures, such as computing architectures that support local, distributed, or cloud-based software platforms, and are suitable for supporting computer system 120.

In some embodiments, computer system 120 is a computing system made up of one or more computing devices. In an embodiment, computer system 120 includes an adaptive multiagent operating system, but it will be appreciated that computer system 120 may also take the form of an adaptive single agent system or a nonagent system. Computer system 120 may be a distributed computing system, a data processing system, a centralized computing system, a single computer such as a desktop or laptop computer, or a networked computing system.

In some embodiments, computer system 120 is a multi-agent computer system with agents. A multiagent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multiagent operating systems, as they relate to these embodiments, is provided in U.S. patent application Ser. No. 13/250,072 (filed Sep. 30, 2011), which is herein incorporated by reference in its entirety.

Figure 2A:
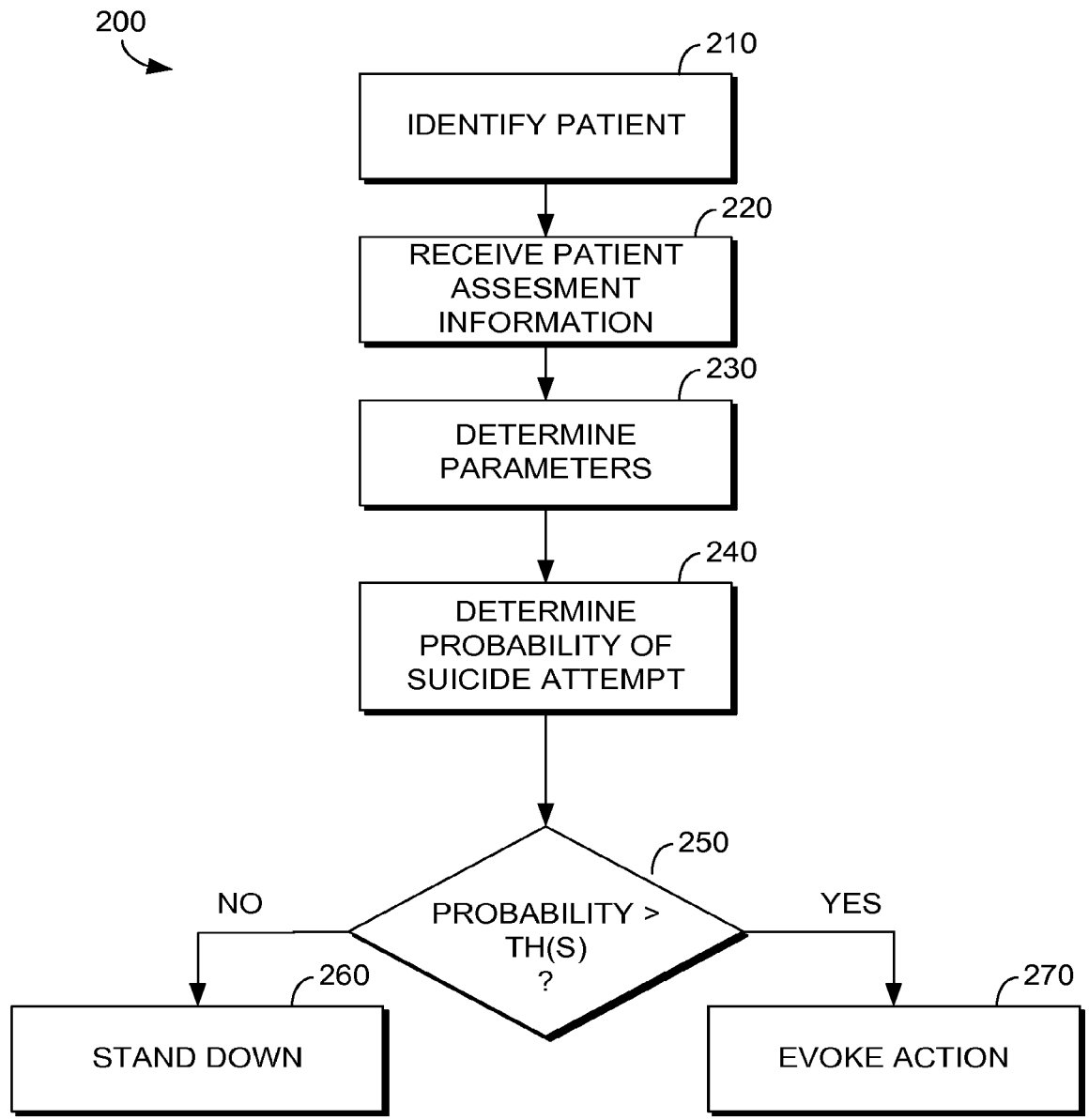
FIGS. 2A, 2B, and 2C depict flow diagrams of embodiments of methods for assessing mental health status and managing the condition of a person at risk for suicide by monitoring measurements of one or more physiologic or activity-related variables.

Referring to FIG. 2A, a flow diagram is provided for an embodiment of a method for managing the mental health conditions of persons at risk for suicide, and which is generally referred to herein as 200. At a step 210, a patient is identified. In an embodiment, a patient is identified as having a diagnosis classified as a mental health condition associated with risk of suicide. In some embodiments, the patient may be an in-patient and in some embodiments, admission assessment orders for the patient are identified. In some embodiments, a patient account, or EHR, is located or accessed.

At a step 220, patient assessment information is received. In some embodiments, the assessment information is received utilizing care provider interface 145. In some embodiments, this information includes the values obtained from a patient assessment application facilitated by care provider interface 145. In some embodiments, the received information also includes identifying information, such as information identifying the patient assessment application, the time of the assessment, the patient, or an account or record associated with the patient. In some embodiments, this information can take the form of a username, password or similar security identifier, or other identifier, and can be used to specify an account or location for storing the received assessment information and for accessing previously received assessment information associated with the patient. In an embodiment, the received information is encrypted or otherwise securely communicated and processed in order to comply with health-care privacy laws and to ensure privacy.

In some embodiments, information received in step 220 is added to an account, which may be associated with the patient and/or appended to previously received assessment information, thereby forming a timeseries. In some embodiments, patient assessment information may be received on a daily basis, using an assessment application such as the example shown in FIG. 3. Here, based on newly received information, a patient's treatment may be reevaluated periodically, such as daily, so that it can be determined whether the patient needs to be moved to an isolation unit or assigned a dedicated nurse for monitoring, for example.

In some embodiments, steps 210 and 220 may repeat or change order. In some embodiments, following receipt of the information in step 220, a confirmation is provided to the patient, user, or caregiver, that the information is received. This confirmation can be important because it provides immediate feedback to the user, and also informs the user that any significant recent changes in condition will be acted upon.

Continuing with step 220, in some embodiments, received assessment information is persisted for later use in prediction of changes in patient status, or prevention of deterioration of mental health status. In some embodiments, only recent measurement information is stored and stale information, including stale timeseries information, is discarded. In some embodiments, the timeseries is persistently stored for research purposes, and in some embodiments, a hash value of a patient's timeseries information is generated for facilitating storing information about the timeseries for later use.

At a step 230, parameters associated with monitoring the patient and determining patient status are determined. In some embodiments, this includes establishing frequencies for data aggregation per monitored variable, such as for example: the number of years chronicity of the patient's current mental health condition; number of prior admissions; suicidal ideation metrics; recent loss or bereavement delusional ideation; and history of family member with completed suicide. In some embodiments, determining parameters further includes determining inactivity-threshold limits for identifying periods of inactivity, wherein a patient's status is not being timely assessed, and determining threshold limits so as to enable notification to caregivers when such thresholds are exceeded, and determining change threshold(s) for allowed changes per measured variable for each mental health condition. In some embodiments, upon exceeding a threshold of inactivity, such as where the time interval since the time a patient was last assessed and that assessment information received, has exceeded a specified inactivity-time interval, then a notification is provided to a caregiver, case manager, health-care provider, or similar entity.

Continuing with step 230, parameters are determined including change threshold(s) for determining the amount of permitted change in variable measurements before evoking an action. A change threshold may be referred to as a decision boundary, transgression boundary, or in cases where there is an upper and lower change threshold, an upper decision boundary (UDB) and a lower decision boundary (LDB), respectively. In some embodiments, a threshold value is determined based on the specific monitored variable(s) of the patient's mental health condition, and may be specified by the health-care provider, insurance provider, caregiver, or device manufacturer, and may be overridden. In some embodiments, a software agent determines the threshold values by accessing a table of threshold values associated with health conditions. In some embodiments, an agent determines the threshold values based on the monitored mental health condition, the patient's health status, timeseries information, or a combination of these. In some embodiments, the threshold is set as an empirical decision model and could be set at a different level based on a predicted likelihood score.

In some embodiments, timeseries information is prepared for the variable being monitored based on assessment information received in step 220. In such embodiments, recently received assessment information, received in step 220, is appended to previously received assessment information, thereby forming a timeseries of measurement values over a period of time. In embodiments where more than one variable is monitored, a timeseries can be prepared for each variable.

At a step 240, the probability that the patient will attempt suicide is determined. In some embodiments, a prediction interval or confidence interval associated with that probability is also determined. A statistical classification model may be employed, in some embodiments, such as for example, logistic regression, support vector machines, neural networks, cluster algorithms, binomial classification models, or other models dealing with a "yes-no" type binomial variable for determining a "yes" or "no" likelihood of a condition and the probability of the determined "yes" or "no." In some embodiments, a cumulative sum (CUSUM) may be utilized. In some embodiments, the determination is facilitated using the R System of software packages 126 described in connection to FIGS. 1A and 1B.

In embodiments employing a logistic regression model, a probability for a patient attempting suicide and a ninety-five percent prediction interval, with N=1, is determined as described previously, where $\beta_1$=ln(OR), $\beta_0$=a default rate of suicides, and OR, the odds ratio from the matrix described below, is given as OR=AD/CB, where A is the count for prediction that a suicide attempt is likely that resulted in a suicide attempt; B is the count for prediction that a suicide attempt is likely that resulted in no suicide attempt; C is the count for prediction that a suicide attempt is not likely that resulted in a suicide attempt; and D is the count for prediction that a suicide attempt is not likely that resulted in no suicide attempt.

With reference to FIG. 4, there is provided an illustrative example calculation of a prediction interval PI, used for determining a patient's likelihood of committing suicide. The example illustratively provided in FIG. 4 was carried out on a system, with reference to FIGS. 1A-1C, comprising a server cluster running the Linux operating system on computer system 120, and the R open-source statistical software services 126. Behavioral health services 122 included Cerner Behavioral Health™ and Healthe Intent™ and a distributed adaptive agent operating system 129 having cloud-based services provided the persistent data storage and retrieval and adaptive agent and time-out and inactivity detection services.

Continuing with FIG. 4, a matrix 402 is shown of numerical counts representing A, B, C, and D, wherein the values of A, B, C, and D are 736, 416, 322, and 480, respectively. The matrix 402 rows "pred_sui+" and "pred_sui−" represent that a suicide attempt is predicted and a suicide attempt is not predicted, respectively. Matrix 402 columns "sui+" and "sui−" represent that there was a suicide and there was not a suicide, respectively. The values of A, B, C, and D represent counts wherein, for example, 736 (the value of A) is a value indicating that the count where predicted probability level in the logistic regression was above a default threshold. Thus similarly, the lower left (C) corresponds to false negatives (suicide attempt not predicted because the default threshold was not exceeded, but an attempted suicide occurred nevertheless.) The upper right (B) corresponds to false positives, where patients were predicted of being at risk for suicide but did not attempt to commit suicide, at least during the time they were monitored.

In embodiments using logistic regression where the default thresholds are set based on an empirical decision model, setting the threshold to different levels, based on predicted likelihood score, will result in different counts or values for A, B, C, and D. Therefore the default threshold(s) may be set to achieve desired specificity and sensitivity. In the example of FIG. 4, which has an observational cohort of 1,954 people, an initial default threshold setting yields relatively balanced counts.

Returning to FIG. 2A, at step 250, the probability determined in step 240 is compared against one or more default thresholds determined in step 230. If the probability is less than the threshold (or a lower bounded threshold value, if there is more than one threshold) then the method proceeds to step 260 and stands down until additional information is received, which might occur following the patient's next assessment session using a patient assessment application. In some embodiments, the system enters a quiescent mode or a sleeping mode.

Returning to step 250, if the probability exceeds a threshold (or an upper bounded threshold value, if there is more than one threshold), then at a step 270, an action is evoked. In some embodiments, evoking an action includes providing a notice that the patient's condition has changed. Notice might be provided to a caregiver, case manager, health-care provider, or other suitable entity. In some embodiments, the action includes an alert, and in some embodiments, the action includes issuing an order or recommending to a health-care provider that an order be used, such as for example, more closely monitoring the patient's condition, assigning a nurse to monitor the patient, or moving the patient into isolation.

Figure 2B:
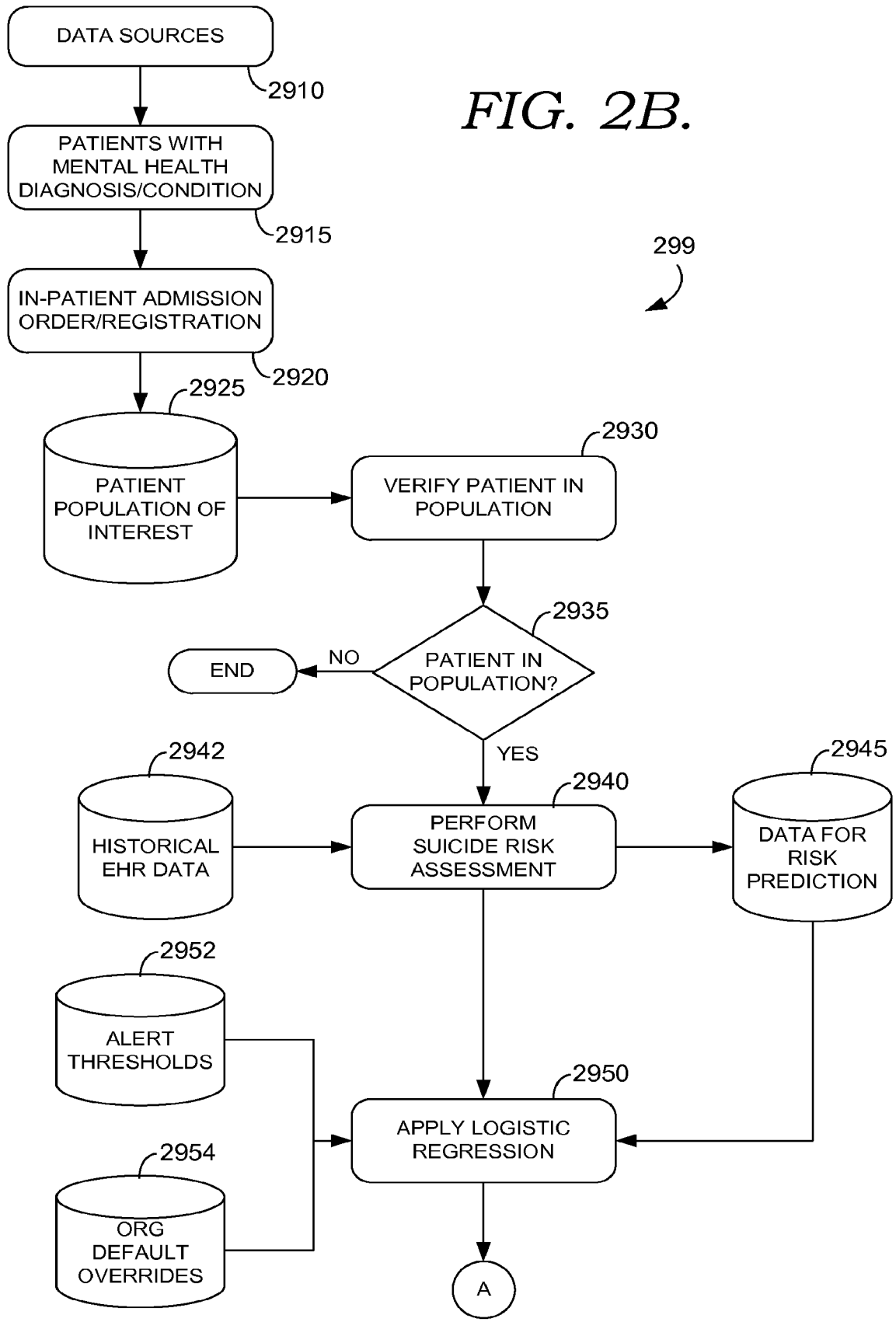
Figure 2C:
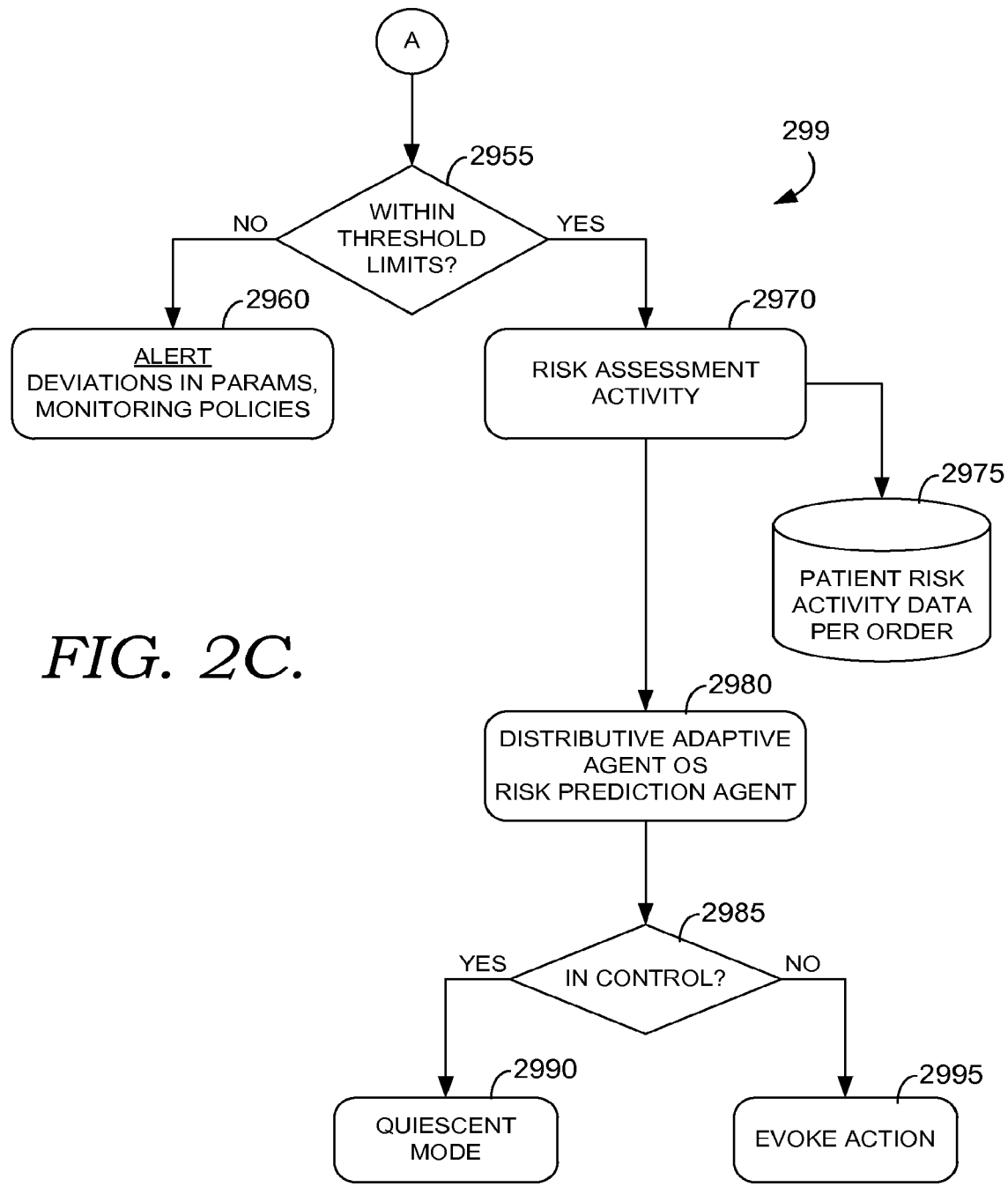

Turning now to FIGS. 2B and 2C, a flow diagram is provided for another embodiment of a method for managing the mental health conditions of persons at risk for suicide, and which is generally referred to herein as 299. Flow diagram of FIGS. 2C and 2D includes data stores, such as data stores 2925, 2942, 2945, 2952, and 2954, illustratively depicted as cylinders, which in some embodiments comprise data store 121. Arrows to or from a data store indicate that information is received from or stored on the data store. In some embodiments, method 299 first verifies that a particular patient is in the population of patients (steps 2910-2935), before proceeding with a suicide risk assessment at step 2940.

At step 2910, data sources are identified including EHRs and patient(s) information data sources. At step 2915, patients with mental health conditions are identified, and at step 2920 in-patient admission order or registration is performed. Accordingly, at 2925, a patient population of interest has been determined. At step 2930 and 2935, a determination is made as to whether a particular target patient is in the patient population of interest. If the patient is not in the population of interest, then some embodiments of method 299 terminate. For example, if the population of interest is patients having mental health conditions with some risk of suicide, and the target patient is not within this population, then the method ends. Similarly, if the population of interest is patients with a likelihood of having sepsis, and the target patient is not diagnosed as having sepsis, then the method ends.

At step 2940 a suicide risk assessment (or assessment for the particular health condition) is performed. Some embodiments of method 299 begin with step 2940. In some embodiments, step 2940 comprises performing an assessment such as described in connection to FIG. 3, and in some embodiments, this comprises an online in-patient suicide risk assessment. In some embodiments, the assessment at step 2940 is based on one or more sensors, such as speech or motion sensors of the target patient, or based on other information received form the patient such as results from having the patient perform an activity or questionnaire. Some embodiments of step 2940 receive historical patient information from data store 2942. Some embodiments of step 2940 determine a prediction risk for suicide, which is illustratively shown as stored in data store 2945. In some embodiments, step 2940 occurs periodically or repeatedly, and previously determined risk predictions are stored at data store 2945.

At step 2950, logistic regression is applied. In some embodiments, the logistic regression is based on the outcome of step 2940 and in some embodiments also based on previous outcomes (received from data store 2945). In some embodiments, alert thresholds are received (as shown from data store 2952) and/or default overrides in thresholds and transgression boundaries (as shown from data store 2954).

Continuing on FIG. 2C, at step 2995 a determination is made as to whether the outcome of the linear regression is within the threshold limits. If no, then at step 2960 an alert or notice is provided. If yes, then at step 2970, in some embodiments, a risk assessment activity may be performed. In some embodiments, step 2970 determines the level of risk and confirms that the target patient is at risk, and/or determined additional information from the patient in order to determine specific orders of care or treatment to intervene. In some embodiments, the outcome of step 2970 is stored at data store 2975, where it may become part of the patient history, in some embodiments.

At step 2980 and 2985, software agent(s), such as a risk prediction agent or software program routines determine whether the patient's condition is under control. In some embodiments, if a the patient's condition is in control, then at a step 2990, the method stands down and waits until additional information is received, such as from step 2940. In some embodiments, the system enters a quiescent mode or a sleeping mode. Where the patient's condition is determined as not in control or degenerating, then at a step 2995, an action is evoked. In some embodiments, an action includes providing a notice that the patient's condition has changed. Notice might be provided to the patient, a caregiver, health-care provider, or other suitable entity. In some embodiments, the action includes an alert, and in some embodiments the action includes issuing an order or recommending to a health-care provider that an order be used, such as for example, more closely monitoring the patient.

FIG. 3 is described above in connection to FIGS. 1A and 1B, and FIG. 4 is described above in connection to FIG. 2A.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. For example, embodiments of the invention may be used to identify emergent changes, including beneficial changes such as changes due to athletic training, psychological or psychiatric treatment, or recovering from a condition that is curable, as well as deterioration, such as someone becoming increasingly mentally ill. In one example, an embodiment may be applied to determine whether or not a patient is at risk for sepsis and an associated confidence interval for that determination.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

Some embodiments of the present invention include methods and computer-readable media having computer-executable instructions embodied thereon for performing a method for monitoring serial quantitative measurements made of one or more demographic and mental health assessment variables in a person, comprising: (a) acquiring and storing measurements from a patient assessment application, which may be in the form of an online software application including an assessment data entry form; (b) transferring periodically the assessment values from the client assessment application to an electronic health record system; (c) detecting whether the measurements of the variable or plurality of variables for the individual patient merits intervention by one or more individuals who are responsible for the care of the person, (d) notifying one or more individuals from a list of individuals who have responsibility for the care of the individual and/or responsibility for risk management and regulatory compliance of the institution, wherein the set may include other caregivers, or one or more health plan case managers or quality or risk-management officers; and (f) tracking and storing a notification event and the status and time of response or nonresponse by the caregiver to the notification.

Some embodiments further include applying statistical patterns involving the variable(s) to determine a likelihood of out-of-control deviations that have materialized, and an elevated probability of attempted suicide such that an in-patient may be interdicted by undertaking appropriate preventive therapeutic or diagnostic actions.

Some embodiments further include wherein a statistical probability of suicide attempt by a patient while an in-patient is determined using a logistic regression model, multivariate partial least squares model, artificial neural network model, Bayesian predictive network model, or other prediction modeling methods such as are known to those practiced in the art.

Some embodiments further include designating and storing, in a persistent reference database an alert, notification, or other communication to be triggered in the event that the system detects a control-limit threshold transgression.

Some embodiments further include retrieving a plurality of monitoring datasets from one of a patient care record for an individual patient, a peer group, and an overall patient population having the same or similar mental health condition against which a comparison may be made.

Some embodiments of the present invention include methods and computer readable media having computer-executable instructions embodied thereon for performing a method for detecting statistically and clinically significant changes in one or more mental health conditions and indicia of the status or severity thereof, comprising: storing a plurality of monitoring sets of recorded measures associated with patient information, wherein the patient information is recorded on an intermittent, recurring, substantially continuous basis; determining a patient status change by comparing a recent recorded measure from at least one of the monitoring sets to the timeseries of previously recorded values of that measure or measures. Some embodiments further include applying a set of indicator thresholds, with each threshold corresponding to a quantifiable measure used to monitor mental health aspects indicative of in-patient suicide risk, comparing a patient status change to an indicator threshold corresponding to the same type of patient information as the at least one recorded measure and the at least one other recorded measure; and evaluating each patient status change against each such further indicator threshold corresponding to the same type of patient information as the recorded measures which were compared.

Some embodiments of the present invention include a system for detecting statistically and clinically significant changes in one or more mental health conditions and indicia of the status or severity thereof, comprising a database storing a plurality of monitoring sets which each comprise recorded measures relating to patient information recorded on an intermittent, recurring, substantially continuous basis; a comparison module for determining a patient status change by comparing at least one most recent recorded measure from at least one of the monitoring sets to the timeseries of previously recorded values of that measure or measures.

Some embodiments further comprise a set of further indicator thresholds, each indicator threshold corresponding to a quantifiable measure used to monitor mental health aspects indicative of in-patient suicide risk. Some embodiments further comprise wherein the comparison module compares each patient status change to each such further indicator threshold corresponding to the same type of patient information as the at least one recorded measure and the at least one other recorded measure, and an analysis module evaluates each patient status change against each such further indicator threshold corresponding to the same type of patient information as the recorded measures that were compared.

Some embodiments of the present invention include methods and computer readable media having computer-executable instructions embodied thereon for performing a method for monitoring and managing in-patient health care at risk for suicide comprising: (a) identifying a patient; (b) receiving patient assessment information from one or more patient assessment application; (c) determining parameters including inactivity thresholds for determining whether or not extended periods of inactivity between successive assessments has occurred, and default thresholds for specifying a level of change permitted for each measured variable; (d) determining a probability of suicide attempt by the patient, which may be in the form of a 95% probability interval, in some embodiments; (e) comparing the determined probability to the default threshold(s); (f) evoking an action if the probability of attempting suicide exceeds the default threshold, wherein the evoked action includes providing a notification indicating that the patient's condition has changed, wherein the notification is provided to at least one of a patient caregiver and health plan case manager; and (g) tracking and storing the notification event and the status and time of response or nonresponse by the patient or caregiver to the notification.

Some embodiments further include wherein the evoked action includes issuing an alert to a care provider, a caregiver, case manager, health-care provider, or entity specified by one of these. Some embodiments further include wherein the alert is an audible alarm, SMS text message, email, phone call or pop-up widow notification. Some embodiments further include wherein the evoked action comprises issuing an order, wherein the order comprises more closely monitoring the patient or moving the patient to isolation.

Some embodiments further include determining statistical patterns involving shift or drift in the mean value of the monitored variable(s) measurement values for detecting the likelihood of out-of-control deviations that have materialized or are imminently likely to materialize. Some embodiments further include determining an elevated probability of the likely benefit that can be expected by undertaking appropriate preventive therapeutic or diagnostic actions, including case managers contacting the patient or caregivers, upon detection of an out-of-control deviation.

Some embodiments further comprise determining a first time interval by performing a comparison of the current date with the date of the most recent patient assessment information that has been received, determining a second time interval corresponding to a maximum time interval permitted between two successive patient assessments, comparing the first and second time interval, and issuing an inactivity alert if the first time interval exceeds the second time interval. Some embodiments further comprise wherein the second time interval is specified by the caregiver or health care provider, and some embodiments further comprise wherein the second time interval is defined based on the patient's condition, or an adjustable interval that is set for the patient, so as to accommodate situational or logistical constraints that affect the regularity with which providing assessment information is practical for the patient to perform.

The invention claimed is:

1. A method to monitor suicide attempts and/or prevent suicide, the method comprising:
    linking, by a computing device, a care provider interface to a patient application, wherein the care provider interface is worn by a patient;
    associating an electronic health record (EHR) of the patient with the patient application, wherein associating includes enabling assessment-application manufacturer-agnostic uploading and analysis so that patient variable values of a particular type are uniformly deposited in the EHR and retrievable for analysis under a unified taxonomy or ontology to enable consistent workflow independent of which software, manufacturer, or measuring device model deposited the patient variable values;
    automatically populating fields of the patient application for the patient with patient variable values obtained from the care provider interface or the EHR;
    accessing, by the computing device, the patient application that includes the patient variable values obtained from the patient over a period of time from the care provider interface worn by the patient, the patient variable values indicating levels of diurnal peak cortisol, trough cortisol, and norepinephrine;
    monitoring, by the computing device, the levels of the diurnal peak cortisol, the trough cortisol, and the norepinephrine by generating a timeseries using the patient variable values from the patient application over the period of time;
    identifying, by the computing device, one or more changes in the levels of diurnal peak cortisol, trough cortisol, and norepinephrine over the period of time based at least in part on the timeseries;
    generating, by the computing device, a predictive score using the one or more changes in the levels of diurnal peak cortisol, trough cortisol, and norepinephrine for the patient, the predictive score indicating a probability of the patient attempting suicide;
    determining, by the computing device, that the predictive score is indicative of deterioration of a mental health condition of the patient based on a comparison of the predictive score with one or more predetermined thresholds, wherein the predictive score is determined using a logistic regression model to facilitate an adjustment to the probability of the patient attempting suicide;
    generating, by the computing device, a notification comprising a response for intervening action to prevent the deterioration of the mental health condition of the patient;
    communicating, by the computing device, the notification to a care provider associated with the patient, wherein the communicating comprises accessing contact information, and receiving confirmation of receipt of the notification from the care provider;
    updating, by the computing device, a data store with the predictive score to facilitate updating the logistic regression model; and
    uploading the mental health condition of the patient to the patient application.

2. The method of claim 1, wherein communicating the notification comprises automatically initiating the response for the intervening action to prevent the deterioration of the mental health condition of the patient.

3. The method of claim 1, wherein communicating the notification comprises issuing or recommending an order for increased monitoring of the mental health condition of the patient, to assign a nurse to monitor the patient, or to move the patient into isolation.

4. The method of claim 1, further comprising determining a plurality of inactivity threshold limits for the patient for identifying periods of inactivity based on times between successive patient assessments.

5. The method of claim 1, further comprising detecting a period of inactivity based on at least one inactivity threshold being satisfied.

6. A system comprising:
    a processor; and
    a non-transitory computer storage medium storing computer-usable instructions that, when used by the processor, cause the processor to perform operations comprising:
    linking a care provider interface to a patient application, wherein the care provider interface is worn by a patient;
    associating an electronic health record (EHR) of the patient with the patient application, wherein associating includes enabling assessment-application manufacturer-agnostic uploading and analysis so that patient variable values of a particular type are uniformly deposited in the EHR and retrievable for analysis under a unified taxonomy or ontology to enable consistent workflow independent of which software, manufacturer, or measuring device model deposited the patient variable values;

automatically populating fields of the patient application for the patient with patient variable values obtained from the care provider interface or the EHR;

accessing the patient application that includes the patient variable values obtained from the patient over a period of time from the care provider interface worn by the patient, the patient variable values indicating levels of diurnal peak cortisol, trough cortisol, and norepinephrine;

monitoring the levels of the diurnal peak cortisol, the trough cortisol, and the norepinephrine by generating a timeseries using the patient variable values from the patient application over the period of time;

identifying one or more changes in the levels of diurnal peak cortisol, trough cortisol, and norepinephrine over the period of time based at least in part on the timeseries;

generating a predictive score using the one or more changes in the levels of diurnal peak cortisol, trough cortisol, and norepinephrine for the patient, the predictive score indicating a probability of the patient attempting suicide;

determining that the predictive score is indicative of deterioration of a mental health condition of the patient based on a comparison of the predictive score with one or more predetermined thresholds, wherein the predictive score is determined using a logistic regression model to facilitate an adjustment to the probability of the patient attempting suicide;

generating a notification comprising a response for intervening action to prevent the deterioration of the mental health condition of the patient;

communicating the notification to a care provider associated with the patient, wherein the communicating comprises accessing contact information and receiving acknowledgement of receipt of the notification from the care provider;

updating a data store with the predictive score to facilitate updating the logistic regression model; and uploading the mental health condition of the patient to the patient application.

7. The system of claim 6, wherein the operation of communicating the notification comprises issuing or recommending an order for increased monitoring of the mental health condition of the patient, to assign a nurse to monitor the patient, or to move the patient into isolation.

8. The system of claim 7, wherein the notification and a status indicating the response to the notification by the care provider or the patient is tracked.

9. The system of claim 6, wherein a plurality of inactivity threshold limits for the patient are determinable for identifying periods of inactivity based on times between successive patient assessments.

10. The system of claim 6, wherein a period of inactivity is detectable based on at least one inactivity threshold being satisfied.

11. One or more non-transitory computer storage media having computer-executable instructions embodied thereon that, when executed by a computer, causes the computer to perform operations for implementing a method to monitor suicide attempts and/or prevent suicide, the operations comprising:

linking a care provider interface to a patient application, wherein the care provider interface is worn by a patient;

associating an electronic health record (EHR) of the patient with the patient application, wherein associating includes enabling assessment-application manufacturer-agnostic uploading and analysis so that patient variable values of a particular type are uniformly deposited in the EHR and retrievable for analysis under a unified taxonomy or ontology to enable consistent workflow independent of which software, manufacturer, or measuring device model deposited the patient variable values;

automatically populating fields of the patient application for the patient with patient variable values obtained from the care provider interface or the EHR;

accessing the patient application that includes the patient variable values obtained from the patient over a period of time from the care provider interface worn by the patient, the patient variable values indicating levels of diurnal peak cortisol, trough cortisol, and norepinephrine;

monitoring the levels of the diurnal peak cortisol, the trough cortisol, and the norepinephrine by generating a timeseries using the patient variable values from the patient application over the period of time;

identifying one or more changes in the levels of diurnal peak cortisol, trough cortisol, and norepinephrine over the period of time based at least in part on the timeseries;

generating a predictive score using the one or more changes in the levels of diurnal peak cortisol, trough cortisol, and norepinephrine for the patient, the predictive score indicating a probability of the patient attempting suicide, wherein the predictive score is determined using a logistic regression model to facilitate an adjustment to the probability of the patient attempting suicide;

determining that the predictive score is indicative of deterioration of a mental health condition of the patient based on a comparison of the predictive score with one or more predetermined thresholds;

generating a notification comprising a response for intervening action to prevent the deterioration of the mental health condition of the patient;

communicating the notification to a computing device of a care provider associated with the patient, wherein the communicating comprises accessing contact information and receiving acknowledgement of receipt of the notification from the care provider;

updating a data store with the predictive score to facilitate updating the logistic regression model; and uploading the mental health condition of the patient to the patient application.

12. The one or more non-transitory computer storage media of claim 11, wherein the predictive score comprises a probability for attempting suicide with a ninety-five percent prediction interval.

13. The one or more non-transitory computer storage media of claim 11, wherein a plurality of inactivity threshold limits for the patient are determinable for identifying periods of inactivity based on times between successive patient assessments.

14. The one or more non-transitory computer storage media of claim 11, wherein a period of inactivity is detectable based on at least one inactivity threshold being satisfied.

15. The one or more non-transitory computer storage media of claim 11, wherein the operation of communicating the notification comprises automatically initiating the response for the intervening action to prevent the deterioration of the mental health condition of the patient.

16. The method of claim 1, wherein the logistic regression model retrieves information from the patient application including at least one of: a default rate of suicides, a prediction that a suicide attempt is likely, or a prediction that the suicide attempt is not likely.

17. The method of claim 1, wherein the patient is in a population of patients that are monitored in geographically distinct locations.

18. The method of claim 1, wherein the period of time is at least once per day.

19. The method of claim 1, wherein the response for intervening action includes at least one of moving the patient into a locked ward, physically restraining the patient, or moving the patient into an increased monitoring-intensity area.

20. The method of claim 1, wherein generating the timeseries further includes determining a change pattern in the timeseries representing a level of change in the patient variable values.

\* \* \* \* \*